(12) United States Patent
Nitsan et al.

(10) Patent No.: US 8,652,102 B2
(45) Date of Patent: Feb. 18, 2014

(54) COLONIC CLEANSING DEVICE

(75) Inventors: David Nitsan, Tel Aviv (IL); Shay Dubi, Tel Aviv (IL)

(73) Assignee: Jet Prep Ltd., Yoqneam (IL)

( * ) Notice: Subject to any disclaimer, the term of this patent is extended or adjusted under 35 U.S.C. 154(b) by 0 days.

(21) Appl. No.: 13/439,043

(22) Filed: Apr. 4, 2012

(65) Prior Publication Data
US 2012/0253284 A1 Oct. 4, 2012

Related U.S. Application Data

(63) Continuation of application No. 12/449,263, filed as application No. PCT/IB2008/050335 on Jan. 30, 2008, now abandoned.

(60) Provisional application No. 60/887,356, filed on Jan. 31, 2007, provisional application No. 61/024,207, filed on Jan. 29, 2008.

(51) Int. Cl.
*A61M 37/00* (2006.01)
(52) U.S. Cl.
USPC ............................................. 604/150
(58) Field of Classification Search
USPC ............................ 604/39, 150, 187, 333, 911
See application file for complete search history.

(56) References Cited

U.S. PATENT DOCUMENTS

| | | | |
|---|---|---|---|
| 4,204,528 A | | 5/1980 | Termanini |
| 4,451,257 A | * | 5/1984 | Atchley .......................... 604/119 |
| 5,203,769 A | * | 4/1993 | Clement et al. ................. 604/32 |
| 5,240,675 A | * | 8/1993 | Wilk et al. ....................... 422/22 |
| 5,630,795 A | * | 5/1997 | Kuramoto et al. ............... 604/30 |
| 2006/0173244 A1 | * | 8/2006 | Boulais et al. ................. 600/156 |
| 2010/0298773 A1 | * | 11/2010 | Nitsan et al. ................... 604/150 |

FOREIGN PATENT DOCUMENTS

WO 2005/104928 11/2005

OTHER PUBLICATIONS

International Search Report for PCT/IB2008/050335, mailed Aug. 29, 2008.
Written Opinion for PCT/IB2008/050335, mailed Aug. 29, 2008.

* cited by examiner

*Primary Examiner* — Theodore Stigell
*Assistant Examiner* — Diva K Chander
(74) *Attorney, Agent, or Firm* — William D. Schmidt; Sorell, Lenna & Schmidt LLP

(57) ABSTRACT

The present invention may provide devices suitable for insertion into a body passage. The devices may include a conduit and a distal head region located at the distal end of said conduit. A plurality of apertures on the surface of said head region and conduit may be used to direct a liquid spray outwards from said device. The apertures may be designed and spatially arranged such that when the device is inserted into a body passage, the liquid spray emitted from said apertures may be capable of both reducing the frictional contact between the device and the walls of said passage and of cleansing said passage of undesired solid and other particulate matter.

21 Claims, 10 Drawing Sheets

COLONIC CLEANSING DEVICE

This application is a continuation of U.S. patent application Ser. No. 12/449,263, filed Jul. 30, 2009, now pending, which is a national phase of International Application No. PCT/IB2008/050335, filed Jan. 30, 2008, which designated the U.S. and claims benefit to U.S. Provisional Application Nos. 60/887,356, filed Jan. 31, 2007, and 61/024,207, filed Jan. 29, 2008. The entire contents of each of which are incorporated herein by reference.

FIELD OF THE INVENTION

The present invention relates to a device used to cleanse the colonic lumen. The device may also be used to locally deliver medications into any portion of the colon.

BACKGROUND OF THE INVENTION

Colorectal cancer is the third most common diagnosed cancer in both men and women and the second leading cause cancer deaths in the U.S.

Colonoscopy and computed tomography colonography (virtual colonoscopy) are accepted methods for evaluation of the colon and screening for colorectal cancer. While the following document will use the term "colonoscopy" for simplicity, it is intended that this term will also include virtual colonoscopy within its range of meaning.

The diagnostic accuracy and the therapeutic safety of colonoscopy depend on the quality of the colonic cleansing or preparation. The ideal preparatory regime for colonoscopy would reliably empty the colon of all fecal material in a rapid fashion without causing damage to the colonic tissues. An ideal preparation would also minimize or eliminate any patient discomfort.

Common preparations for cleansing include diet in combination with a cathartic agent, polyethylene glycol preparations, gut lavage and phosphate preparations (oral sodium phosphate and tablet form of sodium phosphate).

The use of these technologies has significant limitations, including:

Significant inconvenience for the patient. Most patients complain of discomfort and it is not uncommon for patients to report an inability to tolerate the colon-cleansing preparation. Complaints may relate to the unpalatable taste and large volume of the preparation, nausea and vomiting, or abdominal cramping and bloating.

Patient unwillingness to take a bowel preparation is an important barrier to colorectal cancer screening.

In some patients colonic preparation is inadequate, resulting in poor diagnostic accuracy and often requiring a repetition of the preparation and the procedure. Inadequate bowel preparation for colonoscopy can result in missed lesions, cancelled procedures, increased procedural time, and a potential increase in complication rates.

There have also been a number of attempts to develop intra-colonic devices and systems that may be used to cleanse the large intestine prior to colonoscopy. Some of these prior art devices are intended for use in conjunction with colonoscopes; for example, they may be designed to be inserted through the colonoscope working channel or attached externally thereto (e.g. US 2005/261553). In other cases, the cleansing device is constructed as a stand-alone instrument, not requiring the participation of an endoscope. An example of such a device is found in U.S. Pat. No. 4,842,853, which describes an intra-colonic catheter device comprising separate suction and irrigation channels. However, this device is primarily intended for use in colonic irrigation (rather than pre-colonoscopy cleansing), and as such has an expanded head region that is designed to frictionally engage with the colonic wall. While this design permits the device of U.S. Pat. No. 4,842,853 to perform irrigation within the descending colon (as described in the patent), the expanded head region would be problematic for negotiating the 90 degree bends encountered when attempting to move the device in and out of the transverse colon. Consequently, this device does not provide a practical solution to the problem of pre-colonoscopy preparation.

There is therefore a need for a non-traumatic colonic preparation method and/or device, which is able to reliably and safely clean the colon prior to colonoscopy, and which assures adequate preparation and reduces or eliminates the need for oral colonic preparations, thus preventing patient discomfort and side effects such nausea and vomiting. Such a method and device may significantly increase patient compliance for screening colonoscopy, improve the chances for early colorectal cancer detection—and thus improve the survival rate from this disease and improve the accuracy of the colonoscopy procedure due to improved quality of cleansing.

Inflammatory Bowel Disease (IBD), including Crohn's disease and Ulcerative Colitis are prevalent diseases, causing significant morbidity. Treatment of IBD often requires medications such as anti-inflammatory agents, corticosteroids and chemotherapeutic agents which have multiple side-effects when administered orally. This has led to the use of enema administration of selected medications for IBD in an attempt to treat local colonic disease, while reducing side effects in other target organs.

Enema administration of medications for IDB is limited due to the fact that the medication reaches a limited area of the colon, and colonic parts which are distal from the anus, such as the transverse and ascending colon, cannot be treated with this method. This results in a large patient population which cannot be treated by a localized colonic treatment regimen and is thus exposed to the side effects of oral administration.

Thus, there would be a significant clinical advantage if a device were available which could be used to administer medications to remote portions of the colon, especially if this could be performed in a manner which is minimally invasive to the patient and does not require significant patient preparation.

It is a main purpose of the present invention to provide a device which may be used to cleanse the colonic lumen in a reliable and safe manner while preventing or minimizing trauma to the colonic wall.

It is a further purpose of the present invention to provide a device which may also be used for the local administration of therapeutic agents to all parts of the colonic epithelium.

Further aims and objects will become apparent as the description proceeds.

SUMMARY OF THE INVENTION

The present inventors have unexpectedly found that it possible to use a liquid jet spray that exits an elongate catheter-like device through a series of pores or apertures in order to accomplish all three the following tasks:
  a) cleanse the lumen of a body cavity such as the colon;
  b) reduce frictional contact of the catheter-like device with the walls of the body cavity, in order to prevent unplanned, undesirable abrasion of the tissue in the body cavity wall; and c) assist in steering the catheter device through tortuous regions of a body passage, such as the colonic flexures.

Based on this unexpected finding regarding the jet sprays, the present invention provides, in a first aspect, a device suitable for insertion into a body passage, comprising a conduit and a distal head region located at the distal end of said conduit, wherein said conduit and said distal head region comprise at least one common internal lumen, wherein said at least one common internal lumen is in fluid communication with a plurality of apertures that are located on the external surface of both the conduit and distal head region, wherein at least some of the apertures in the conduit and distal head region are adapted such that a fluid pumped through said at least one lumen in a proximal-to-distal direction would exit said apertures in the form of a jet spray.

The term 'jet spray' is used herein to indicate the manner in which a body of pressurized liquid exits a small aperture at accelerated speed. The term includes within its semantic range all forms of such liquid jets, for example, fine linear jets, diverging, conical sprays and so on. This aspect will be discussed in more detail hereinbelow.

It should also be noted that the term 'distal' as used throughout this disclosure is taken to refer to the direction away from the operator and into the subject's body. Thus, when used to describe an extremity of a device or instrument (e.g. colonoscope), the terms "distal portion" and the like refer to those parts of said devices and instruments which will be inserted the furthest into the colon or other body passage. The term 'proximal' thus refers to the opposite direction, orientation or region.

In one preferred embodiment of the above-disclosed device, the jet spray apertures are spatially arranged such that if the device were to be placed in a body passage and a jet spray caused to exit said jet spray apertures, said device would be caused to have minimal contact with the walls of said body passage.

Ideally, in order to achieve minimal frictional contact with the internal walls of a body passage (or of any other essentially tubular structure), the jet spray apertures should be arranged in an organized, balanced way, such that the device jet sprays would exert an essentially equal force in all directions if the device were theoretically to be placed along the central longitudinal axis of a hollow tubular structure. Consequently, in one preferred embodiment, the jet spray apertures of the device are arranged in a substantially symmetrical manner around the circumference of an imaginary transverse section of said device. Similarly, in another preferred embodiment, the jet spray apertures are arranged such that at least one of said apertures is to be found in each of the four quadrants of the circumference of an imaginary transverse section of said device, wherein a quadrant may be defined as a sector of a circle that is equal to one quarter of the circumference of said circle.

In order for the device to be able remove the introduced cleaning fluid, said device, in some preferred embodiments at least some of the apertures in the conduit and distal head region are capable of aspirating a liquid situated external to said device upon connection of a negative pressure source to the one or more lumens connected to said apertures.

Whereas in many cases, the liquid jet spray created by the device of the present invention is sufficient for breaking down and removing all of the undesired solid and particulate matter (e.g. fecal material) within the body passage, in some preferred embodiment, the device further comprises mechanical cleaning elements attached to the conduit and/or distal head region. Many such mechanical cleaning elements may be employed discs, brushes, disc brushes, bristles and fabric strips.

It is to be recognized that while the use of the aforementioned ancillary mechanical cleaning elements is desirable in certain circumstances, it is most important that said elements do not increase the frictional contact of the device of the invention with the tissues of the body passage wall during the insertion and advancement of said device into and through the body passage. Consequently, in a preferred embodiment, said elements are constructed such that they do not increase the overall diameter of the distal head region of the device. As a result, in some cases, it may prove necessary to bring the distal head region, together with its attached mechanical cleaning means, into close apposition with a selected region of the body passage wall for the purpose of increasing the cleaning efficiency in that region. Thus, in one preferred embodiment, the device of the invention further comprises guiding means for changing the spatial location of the distal head region. While many such guiding means are possible, in a particularly preferred embodiment, these means comprise one or more wires attached to the distal head region. These wires are threaded proximally (as will be discussed in more detail hereinbelow), such that they can be manipulated by the operator in order to bend the distal portion of the conduit of the device, thereby changing the spatial orientation of the distal head region (in a manner similar to the operation of the control wires of a conventional colonoscope).

In one preferred embodiment of the invention, the device comprises two internal lumens, one of which will usually be used as an aspiration (suction) channel, while the other lumen will be used to bring pressurized cleaning liquid to the spray jet apertures.

In other embodiments, the device may comprise several additional channels for the purpose of conveying various tools, instruments, cables, wires and the like. These elements will be described in more detail hereinbelow. In addition, in some preferred embodiments the presently disclosed device further comprises one or more cameras attached to its external surface, and/or optical fiber bundles for the purposes of illumination. Some of these elements will be provided with their own, dedicated channel, while others (such as endoscopic biopsy instruments) may be inserted through a shared, general working channel, similar to the working channel found in conventional colonoscopes.

In one preferred embodiment of the device, the apertures are located in both the distal head region and along the entire length of the conduit that is attached thereto. In other preferred embodiments, the apertures are present in the head region and over part of the length of the conduit (e.g. at least 50%, at least 20%, less than 20% of the overall conduit length).

In another aspect, the present invention also provides a method for cleansing the lumen of a body passage in a mammalian subject, comprising the steps of:

a) introducing a device according to any of the previous claims into said body passage;

b) connecting a pressurized cleaning fluid supply and negative pressure source to the proximal end of the conduit of said device, such that fluid jet spray exiting the jet spray apertures cause the distal head region and at least part of said conduit to hover within the body passage lumen with minimal contact with the walls therefore, and such that said fluid jet spray causes displacement, dislodgement, disintegration and/or dissolution of solid matter present within said body passage, and such that the jet spray liquid and solid and particulate matter within said body passage is removed from the lumen thereof by aspiration through at least some of the apertures in said device;

c) applying manual pushing and pulling forces to the proximal end of the conduit such that said device advances distally within said body passage;

d) optionally performing further procedures within the body cavity, e) removing said device from said body passage.

Many different procedures may be performed in step (d) of this method. However, in a preferred embodiment, these optionally-performed procedures are selected from the group consisting of tissue biopsy, surgical removal of polyps and other lesions, capture of video and still images of the colonic wall and lumen, and guiding the distal head region towards selected portions of the colonic wall in order to increase cleansing efficiency.

The present invention also provides a method for cleansing the lumen of a body passage in a mammalian subject, comprising the steps of:

a) inserting an endoscope into said body passage;

b) inserting a device according to any one of claims 1 to 15 into the working channel of the colonoscope;

c) advancing said device through said working channel until the distal head thereof exits the distal end of said working channel, by means of manual pushing and pulling, and optionally by means of connecting the pressurized cleaning fluid supply and negative (suction) pressure source to the conduit of the device, such that the head region and at least part of the conduit are caused to float or hover within the working channel of the colonoscope, thereby significantly reducing frictional contact between the device and the walls of said working channel during the advancement of the device;

d) cleaning the region of the colon that is adjacent to the distal head region and portion of the conduit that has exited the distal end of the working channel of the colonoscope, using the fluid jets and suction created by that region of the device;

e) advancing the colonoscope distally to a new region of interest;

f) repeating steps (c) to (e), as required;

g) removing said device from said body passage.

Although the above-defined methods may be used in many different body passages, in a particularly preferred embodiment, the body passage is the colon, particularly the human colon. In many cases, the methods will be used prior to a colonoscopic procedure (diagnostic and/or operative).

In another aspect, the present invention also provides a system for colonic cleansing comprising:

a) a device as disclosed hereinabove and described in more detail hereinbelow;

b) a pump suitable for causing a cleaning fluid to pass distally through one or more lumens of said device and to exit through a plurality of jet spray apertures;

c) a negative pressure source; and d) optionally further comprising a user interface for controlling the operation of said device, said pump and said negative pressure source.

BRIEF DESCRIPTION OF THE DRAWINGS

The present invention is illustrated by way of example in the figures of the accompanying drawings, in which like references indicate similar elements and in which.

DETAILED DESCRIPTION OF PREFERRED EMBODIMENTS

Figure 1A:
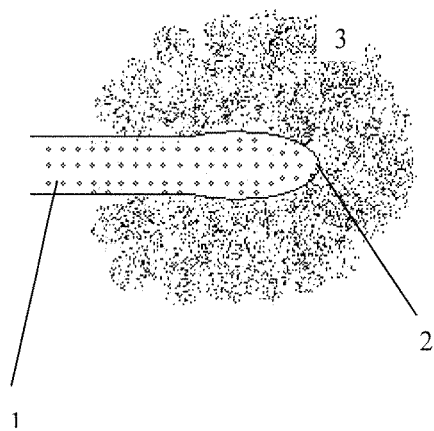
FIGS. 1A and 1B schematically illustrate (respectively) a generalized distal head region and specific, exemplary distal head region of the present invention.

The device defined above is essentially a catheter, connected at its proximal end to a specialized pump which can pump fluid forward within a lumen of the catheter, and pump fluid backward through a different (or the same in another embodiment) lumen of the catheter. The anterior pumping action supplies fluid that functions both as a fecal dematerialization and degradation agent, allowing easier removal of fecal material, and as a catheter driving and maneuvering agent, as will be further explained in the text. The catheter is inserted into the colon through the rectum and anal canal. After insertion the device is advanced distally into the colon by the operator. The device is able to advance within the colon without friction with the colonic walls, it is able to maneuver the tortuosity of the colon and cleanse the colon from all fecal material. The device is also able to administer medications into any part of the colon, within the "forward flow" fluid pumped into the catheter. The device is also able to collect material from any area within the colon, within the "backward flow" fluid pumped from the colon, and is thus enables, for the first time, to search for tumor markers, or other biologic markers, from within the colonic lumen.

In order to meet the aforementioned needs, the device is required to overcome the following challenges and barriers:

Being able to advance through the tortuous colon.

Pushing forces are not always directed in the same direction as the advancement of the device. For example, when the distal head of the device is located in the ascending colon its advancement is directed downwards (towards the legs of the patient), while the operator pushes the device with forces directed upwards (into the anal canal, and towards the head of the patient).

The device may require high pushing forces in order to advance if any friction is caused between the device and the colon wall.

Perforation of the colon must be prevented.

Fecal material must be removed during the procedure.

The device should be simple to use in order to achieve acceptance by the operating physicians, and should be able to advance without requiring any unique imaging modalities.

In order to address all these challenges, the present invention provides a novel type of catheter which can be inserted into a lumen and "floats" or hovers within the lumen by utilizing jets of fluids from the head and from intermittent elements of the catheter, which serve as a propulsion mechanism. The jets of fluid apply a force that prevents the head of the catheter and the body of the catheter from approximating and contacting with the walls of the lumen. When a part of the catheter is closer to the wall of the lumen, the force applied on it due to the jet increases, thus directing the catheter away from the wall of the lumen. Thus the catheter essentially "floats" or hovers within the lumen, without directly contacting the lumen walls and with minimal friction between the catheter and the lumen wall. The same concept is applied in turns or tortuous parts of the colon, where the fluid jets direct the catheter away from the lumen walls and essentially drive and direct the catheter within the lumen. The same concept is applied when the catheter is headed in a different direction than the forces applied by the operator—since the friction is minimal and the catheter hovers within the lumen, it is advanced distally despite the different directions, due to the forces applied by the fluid jets.

The invention thus provides a novel type of catheter in which fluid jets applied through apertures in the catheter prevent the catheter from touching the borders of the intracolonic lumen at all times, and thus will control the advancement within the lumen, allowing bends and turns and preventing bowel perforation. This will also ensure that the force required to advance the catheter is minimal, since the friction is minimal due to the "flotation" of the device within the lumen. The fluid streams will, at the same time, assist with the materialization/shredding of the fecal material.

The shredded material and fluid is, at the same time, suctioned into the lumen of a second lumen of the catheter and is thus removed from the body.

Thus, the device of the invention may be used in order to cleanse and prepare the bowels for colonoscopy without requiring oral preparations, it may be used to collect material samples from any area of the colon (for example, in order to search for tumor markers), and it may be used to apply medications directly and locally to any part of the colon.

As a general remark, the description in the text refers to use of the device of the invention within the colonic lumen, however this is for demonstration only, and the scope of the invention is intended for a wider and broader use and application of such a "floating" or hovering catheter within a lumen of the body, as can be thought of by people experienced in the art. Other examples, which will not be further elaborated in the text, are use in the upper GI system (for example the esophagus, stomach and small intestines), in the urinary system (for example, in the urinary bladder and ureters), in the cardio-vascular system (for example, in veins, arteries, or the chambers of the heart).

The present invention is thus primarily directed to a catheter-like device and method for cleaning a body cavity (such as the colon) in a non-traumatic manner. One of the key features of the present invention is that the novel structure of the device permits advancement through the body cavity in a manner which prevents undesired frictional contact with the walls of that cavity. This feature confers two significant advantages on the present invention: firstly, by means of hovering mechanism, the device centers itself within the body passage, thereby preventing trauma to the surrounding tissues (e.g. intestinal wall) that would otherwise occur. Secondly, the aforementioned hovering mechanism permits the device to be advanced through highly-tortuous body passages such as the colon without causing trauma to the wall of the lumen when negotiating tight bends (e.g. when entering or leaving the transverse colon).

The aforementioned hovering or floating of the device of the present invention is achieved by the use of fluid jets that are formed by pumping a liquid through a series of apertures or nozzles formed in both the distal head and the conduit of the device. It should be noted that in addition to their guidance function (i.e. in causing the device to hover or float), the fluid jets are also responsible for the primary cleaning action of the device. Furthermore, in addition to its cleansing function, the device of the present invention may also be used to extract material from the lumen (e.g. tumor markers) and deliver fluid thereinto (e.g. therapeutic agents).

In a preferred embodiment of the invention the device is a catheter in which fluid jets applied through apertures in the catheter prevent the catheter from touching the borders of the lumen at all times, essentially causing the catheter to float or hover within the lumen, thereby permitting advancement through tortuous bends and turns and so preventing perforation of the lumen wall. This will also ensure that the force required to advance the catheter is minimal, since the friction is minimal due to the flotation or hovering of the device within the lumen. The fluid streams can, at the same time, assist with materialization and shredding of material within the lumen. The catheter may then extract the material from the lumen, thus cleansing the lumen, and collect samples from the lumen. In addition, the catheter can administer specific material, such as medication, into the lumen.

As mentioned hereinabove, in one aspect, the present invention is directed to a method for cleansing the lumen and lumen walls of a body cavity. In one preferred embodiment, the body cavity to be cleaned is the large intestine, more specifically, the colon. In one particularly preferred embodiment, the cleansing method of the present invention is used to clean and prepare the colonic lumen for colonoscopy. The present invention further provides methods for collecting material from the colon, and/or delivering therapeutic agents thereto.

The fluid jet streams applied by the device may comprise any type of appropriate fluid, as is well known to the skilled artisan in this field, including (but not limited to) water, saline, cathartic agents, polyethylene glycol, phosphate preparations and therapeutic agents such as chemotherapy agents (for example Xeloda, Oxaliplatin and CPT) and biologic solutions (for example Erbitux and Avastin).

The aforementioned cleaning fluids and/or therapeutic agents are supplied from an external reservoir and pumped through the conduit to the distal head region of the present invention by means of a pumping device connected to one or more of the lumens in said conduit, such that a fluid spray or jet is created when said fluids leave the device through the apertures (jet nozzles) located in both the head region and conduit. Suitable pressure values generated by the pumping device are in the general range of about 1-5 atm at the device inlet and about 1-3 atm in the distal part of the device. The reduction in pressure between the proximal and distal ends of the device is due to losses along the channels. The flow rate generated by this pressure may be between 4-40 ml/sec. Any suitable pumping device (including—but not limited to—simple water pumps, centrifugal, and peristaltic pumps etc.), as are well known to the skilled artisan in this field, may be used in conjunction with the present invention. An example of a suitable peristaltic pump is the Watson-Marlow Bredel Process Pump model 520S/REH (a manual control high pressure pump generating 60-100 PSI).

Similarly, the proximal end of the suction lumen of the presently disclosed device is connected to a negative pressure source, such as an appropriate water pump, vacuum pump, and so on. The suction pressure is generally in the range of −50 mmHg to −680 mmHg, with an aspiration flow rate in the range of 6-50 liters per minute. Examples of suitable commercially-available vacuum pumps include Vario 9 (low pressure) and Dominant 50 pumps, both produced by Medela of Switzerland.

The pumping device and suction source may be provided as two separate units connected to the proximal end of the conduit of the device of the present invention. Alternatively, these two elements may be integrated into a unified console that may optionally also contain control elements for regulating cleaning fluid and aspiration pressure. Such a console may also optionally provide a light source for optical fiber illumination as well as electrical and data connections for on-board cameras and electrical and mechanical connections for biopsy and surgical instrumentation and directional control wires.

Exemplary materials for construction of the device of the invention are plastic material of various kinds, elastomers and polymers such as silicon, polyurethane, nylon, Pebax, blend of nylon and Pebax. The catheter may include both elastic and non elastic materials.

FIG. 1A is a schematic diagram illustrating the general structure of the device of the present invention. It may be seen from this diagram that the device comprises a head region 2 ("head"—referring to the distal part of the catheter, which is the first part inserted into the lumen) and a conduit 1 connected to the proximal side of said head. The lumen of said conduit 1 is continuous with the lumen of said head region 2. It may also be seen that both the head region and conduit are perforated by a plurality of apertures through which jets of fluid 3 may be produced. The apertures may be of different dimensions and structures, different numbers and geometrical arrangement, and may cover the whole or part of both the distal head region and the conduit. In one preferred embodiment, the apertures are located along the entire length of the conduit. In another preferred embodiment, the apertures are present along at least half of the length of the conduit. In yet another preferred embodiment, the apertures are present along at least 20% of the length of the conduit. In other embodiments, less than 20% of the length of the conduit contain apertures. It is to be emphasized that the presence of the apertures along at least a portion of the conduit (in addition to the distal head region) is a key feature of the present invention. The functional significance of this feature is that the emission of a fluid jet or spray from apertures in the conduit prevents or reduces friction between said conduit and the body cavity wall during the insertion and/or removal of the device in and out of the body cavity (e.g. colon).

The apertures shown in the generalized structure shown in FIG. 1A may be function as fluid jet outlets only, or as suction inlets only, or may be dual-purpose apertures. In the case of dedicated apertures, one or more lumens within the distal head region and conduit convey fluid to the fluid jet outlets, while one or more additional lumens will convey fluid aspirated through the suction inlets. Different exemplary arrangements of the lumens in the conduit of the present invention will be discussed hereinbelow, with reference to FIGS. 4A to 4C.

Figure 1B:
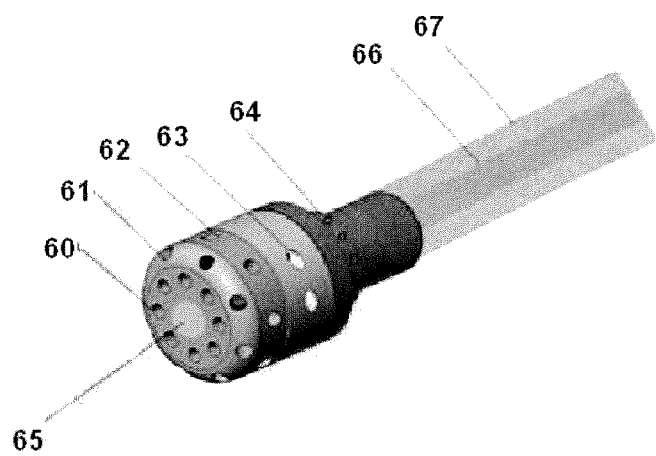

FIG. 1B illustrates one preferred embodiment of the distal head region of the device of the present invention. In this specific embodiment, the head region comprises several different sets of apertures, each with a specific function. Thus, the distal face of the device is perforated by a series of forward-pointing jets 60, the purpose of which is to cleanse the lumen of the colon (or other body cavity) distal to the leading edge of the device. A second set of jet nozzles 61 located within the angled front edge of the device are directed at angle other than 90 degrees to the distal face of the head region, such that in situ they cause a fluid spray to be directed outwards towards the body cavity (e.g. colonic) wall. A third set of jet nozzles 62 which face radially outwards contribute both to the hovering or floating of the head region within the body cavity lumen with minimal friction with the walls of said lumen, and to the disintegration of fecal material lining said walls. In this particular embodiment, a rotatable ring perforated by a series of apertures 63 is located proximally to the nozzles 62. The force of the water ejected from said apertures 63 is sufficient to cause said ring to rotate and thus propel the washing liquids radially outwards with increased force. A further set of apertures 64 are located on the proximal side of head region. In this case, said apertures are directed in a proximal direction, and assist both in the forward (i.e. distal) movement of the device of the invention as well as in the breaking up of fecal material. Returning now to the distal face of the head region, a single, large suction aperture 65 may be seen. This aperture is connected to an aspiration lumen (shown as 66 running through the center of the conduit). The large diameter aperture permits the efficient evacuation of large volumes of cleaning fluid and particulate matter that has been generated as a result of disintegration of fecal material. Finally, a second, outer lumen 67 passing along the conduit is responsible for delivering the pressurized cleaning liquid to the various outlet nozzles 61 to 64, described above.

Figure 1C:
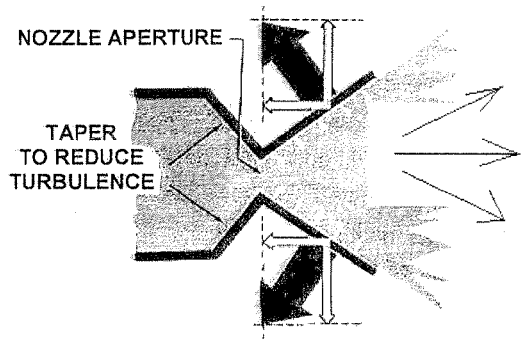
FIG. 1C schematically illustrates certain aspects of the design of the fluid jet nozzles.
Figure 1C:
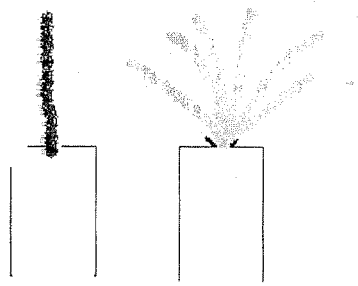

Various different types of nozzle structure may be used in order to optimize flow and to reduce turbulent flow, as well as to determine the desired shape and size of the fluid droplets and exit angle of the spray that leaves the nozzle. For example, the fluid may be directed such that it exits the nozzle as a fine, pointed linear jet. Alternatively, the nozzle may be designed such that the fluid spray leaving therefrom may be conical in shape, with predetermined opening angles, for example 60, 90 or (fully opened) 360 degrees. Both the linear jet and the conical sprays are illustrated in the lower part of FIG. 1C. Two of the nozzle geometry considerations (i.e. size of nozzle aperture, and the use of a pre-constriction taper in order to reduce turbulent flow) that are important in determining the shape and size of the fluid spray are shown in the upper part of FIG. 1C. Clearly, the size and shape of the fluid jets leaving the nozzles may have a large impact on the type of washing forces that may be exerted on the colonic wall. For example, a very fine jet, leaving the nozzle under high pressure will be very effective at dislodging stubbornly-attached, hard fecal matter, albeit over a relatively small surface area. Conversely, nozzles producing larger surface impacts with larger quantities of liquid may be used to wash softer feces in a faster and more efficient manner.

The device may be designed, configured, and constructed from with a single, unitary, tube, followed by the removal, for example, by mechanical cutters or by laser cutting, selected material from the tube, until only the desired geometry, shape, and dimensions of the tube and the apertures remain. There are several potential manufacturing approaches for manufacturing of the device of the invention, and one exemplary manufacturing approach comprises the steps of:

Step 1. Catheter tubes are manufactures by extrusion.
Step 2. Once a tube is formed, it will be cut to acquire the desired length and shape.
Step 3. Apertures are made at different areas of the catheter, as previously described.
Step 4. Connectors will be connected to the catheter proximal end, for example by ultrasonic welding.

Parts of the device (e.g. the distal head components) can be manufactured, for example, by injection molding, which involves heating & injecting plastic material under pressure into a closed metal mould tool. The molten plastic cools & hardens into the shape inside the mould tool, which then opens to allow the moldings to be removed.

The device of the invention may additionally contain several means for viewing the colonic mucosa, and accessing and treating the area (not shown in the figures): for example, a camera (such as a CCD (charge-coupled device) video camera) can be installed on the external wall of the distal head region and/or fiber-optics may be used in order to view and illuminate the colon. In addition other devices may be inserted through the device of the invention and into the colon, for example grasping and cutting elements, in order to allow treatment of the colon, such as removal of colonic tissue for biopsy or cutting and removing colonic tumors. The aforementioned elements and devices may be introduced through a general "working channel" (similar to a colonoscopic working channel) within the conduit. Alternatively, they may have each have their own dedicated lumens within the conduit. A typical example of a device of the present invention fitted with a fiber-optic illumination system and camera is described in more detail hereinbelow.

Exemplary dimensions of the device of the conduit of the invention are as follows. The length is in the range of between about 20 cm and about 200 cm, preferably, about 150 cm. The diameter is in the range of between about 0.2 cm and about 1.5 cm, preferably, about 0.5 cm. The wall thickness of the material of the device is in the range of between about 0.01 mm (10 microns) and about 1.0 mm (1000 microns), preferably, about 0.5 mm (500 microns).

Figure 2:
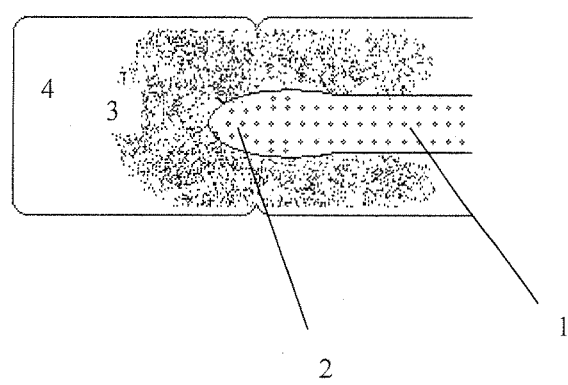
FIG. 2 schematically illustrates an exemplary head section of an embodiment of the invention within the lumen of a body cavity.

Referring again to the drawings, FIG. 2 is a schematic diagram illustrating an exemplary head section 2 and the distal portion of the conduit 1 of an exemplary embodiment of the invention within the lumen of a body passage 4, showing a plurality of apertures, from which jets of fluid 3 are emitted around the catheter. As illustrated, the catheter head 2 is kept in a relatively central area of the lumen 4, away from the walls of the body passage, by means of the fluid jets 3 which apply forces on the walls, causing "hovering" or "floating" of both the head and conduit of the device within the lumen.

Figure 3:
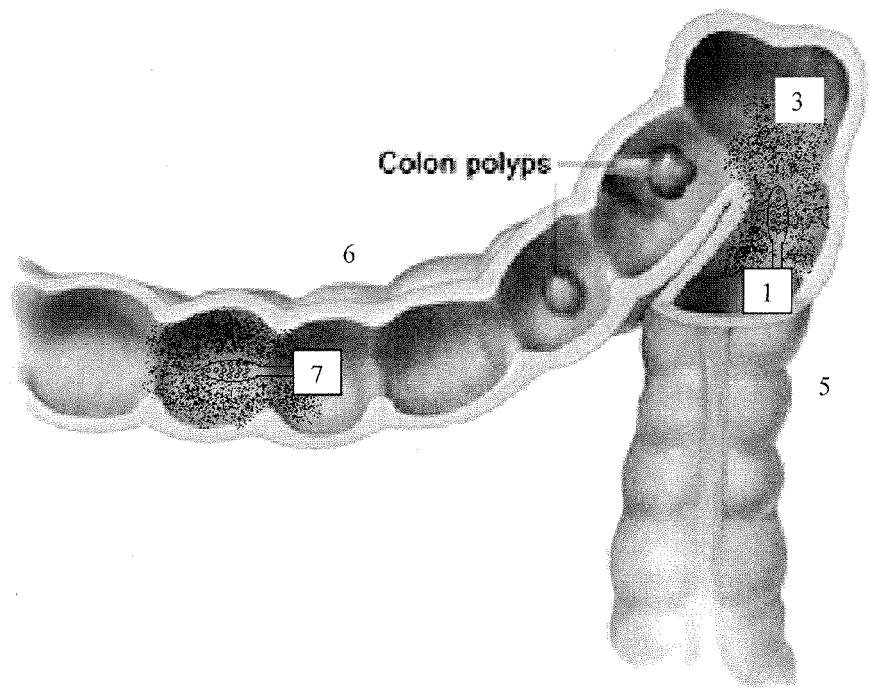
FIG. 3 illustrates an exemplary head section of an embodiment of the invention in use within the colon.

Referring again to the drawings, FIG. 3 is a schematic diagram illustrating an exemplary head section and distal portion of the conduit 1 of an exemplary embodiment of the invention in use within the colon. The device of the invention is representatively shown in two different areas of the colon, in order to illustrate advancement of the catheter. Colonic areas are shown according to the following numbers: Descending colon 5, Transverse colon 6. Towards the right of the figure, the head and distal portion of the conduit 1 of the device of the invention are seen in the upper portion of the descending colon 5, illustrating that fluid jets 3 maintain the device within a relatively central area of the colon, allowing advancement with minimal friction and preventing the catheter from approximating the colonic walls, thus preventing a risk of perforation and allowing advancement through tortuous areas and turns without a need to "actively" navigate the catheter. Following advancement of the device and negotiation of the left colic flexure, the device (here labeled as 7) is now seen in the transverse colon 6. Once more, it may be seen that the fluid jets 3 maintain the device 7 within a relatively central area of the colon. The proximal parts of the catheter are not shown in the drawing.

Figure 4A:
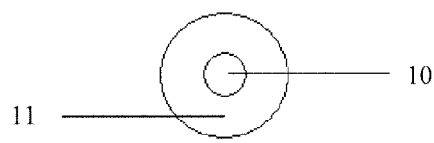
FIGS. 4A, 4B and 4C schematically illustrate cross sections of exemplary embodiments of the invention.
Figure 4B:
Figure 4C:
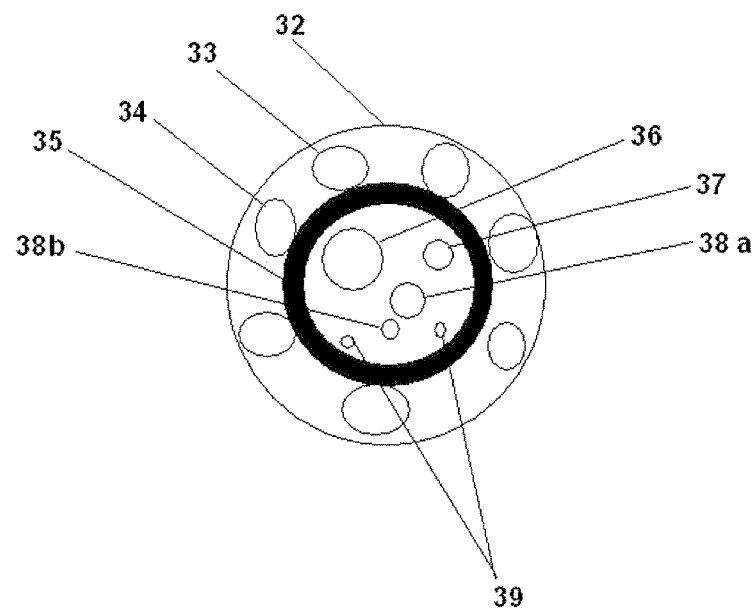

FIGS. 4A, 4B and 4C are schematic diagrams illustrating cross sectional views of exemplary embodiments of the conduit of the invention. FIG. 4A illustrates an embodiment with two lumens, an internal lumen 10 and an external lumen 11. In one exemplary embodiment the flow in the internal lumen is directed distally (forward) towards the head of the catheter conduit, and the flow in the outer lumen is directed proximally (backwards) towards the pump. Thus, when the device of the invention is used in the colon, the fluid in the internal lumen is used to allow the head of the catheter to float or hover within the lumen and to dematerialize the fecal matter within the colon. The debris and fluid from the colon are then removed from the colon through the external lumen and into a drainage system outside of the body.

In another embodiment of the device, the directions of flow may be in the opposite direction to that described above.

FIG. 4B illustrates an additional embodiment of the device in which the lumens of the catheter, shown as 12 and 13, are arranged in a side-to-side manner. In this embodiment, one lumen carries the forward (rinsing fluid) flow into the colon, while the second lumen carries the backward flow of debris and waste water from the colon.

The direction of flow in each lumen may be changed by altering the settings or connections of the fluid pump that is connected to the proximal end of the conduit of the device.

In an additional embodiment of the device of the invention, the two lumen are not a single bi-lumen catheter, but two separate single lumen catheters, which can be inserted into the colon sequentially, one after the other. For example, a first catheter with forward flow is inserted into the colon and used to float or hover the head and allow insertion and dematerialization of fecal matter, and a second catheter is inserted using the first catheter as a track for insertion and this second lumen is used to excrete the fluid and debris from the colon and into an external drainage system.

In another embodiment, the device contains more than two lumens, with one or more lumens used for distal flow and one or more lumens used for proximal flow.

In a still further embodiment, the device may contain only a single lumen used alternately for both distal flow (i.e. provision of cleaning fluid to the outlet nozzles) and for proximal flow (i.e. for the purpose of aspirating and removing fluid and particulate matter).

In another embodiment of the device, the direction of flow within each lumen can be changed during the procedure.

FIG. 4C is a cross-sectional view of a further preferred embodiment of the conduit portion of the device of the present invention. As described hereinabove, in certain cases, the device of the present invention may, in addition to the jet nozzles also comprise certain other functional elements including a camera, a fiber optic light source and surgical tools for biopsy and operative procedures. Some of these elements may be connected to the relevant console (e.g. to provide electrical connections, light source, data channels etc.) by way of a general purpose lumen, similar to the working channel of a conventional colonoscope. Other elements may pass along the length of the conduit of the device by way of dedicated channels. Thus, FIG. 4C depicts a multi-lumen implementation of the device of the present invention, based on a conduit comprising two concentrically placed tubes, an inner tube 35 (e.g. of diameter 12.8 mm) and an outer tube 32 (having a typical diameter in the range of 13-16 mm). As shown in the figure, various different channels are contained within the two main lumens defined by these two tubes. Thus, the outer, toroidal lumen (i.e. the space between the inner and outer tubes) contains a plurality of suction channels 33 and cleaning fluid channels 34 (for the purposes of both causing the device to hover and irrigation/breakdown of the fecal material within the colonic lumen). Both of these two types of channel will typically have diameters in the range of 0.1 to 3 mm. As shown in the figure, the inner main lumen (contained entirely within the inner tube 35 may contain a working channel 36. Typically, such a general purpose working channel will have a diameter of 3.8 mm, and may be used for introducing surgical instruments, such as cutting and grasping tools, for the purpose of obtaining biopsy samples and the surgical removal of tumors. In addition, the inner main lumen may also contain a dedicated channel 38a for the data and power channel of a camera (e.g. a charged-couple device (CCD) video camera, such as manufactured by Pentax) mounted on the external surface of the distal head region. Similarly, a light source optical fiber channel 38b may also be present. The figure also depicts two directing wires 39, as well as an additional small diameter channel 37 for inflating balloon-like elements positioned on or close to the distal head region.

Figure 5:
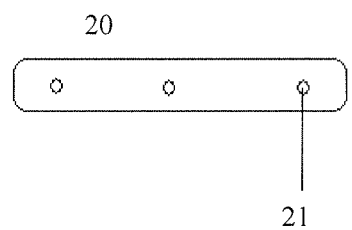
FIG. 5 schematically illustrates a side view of an exemplary embodiment of the invention.

Referring again to the drawings, FIG. 5 is a schematic diagram illustrating a side view of an exemplary embodiment of the invention. A device of the invention 20 is shown, having lateral apertures (side holes) 21. This is to illustrate that the device of the invention may have one or more apertures, preferably multiple apertures, on its external surface. These apertures may be present on the lateral surfaces of both the head region of the device and the lateral surfaces of the conduit, proximal to said head region. Fluid may flow out of these apertures, and serve for both applying force on the colonic lumen—thus assisting with flotation or hovering of the catheter, preventing contact between the catheter and the colonic wall, and reducing friction between the catheter and colonic wall, and for breaking down fecal matter. The presence of the lateral apertures in the catheter body allows flotation and low-friction advancement of the body of the catheter, following the head of the catheter.

Figure 6:
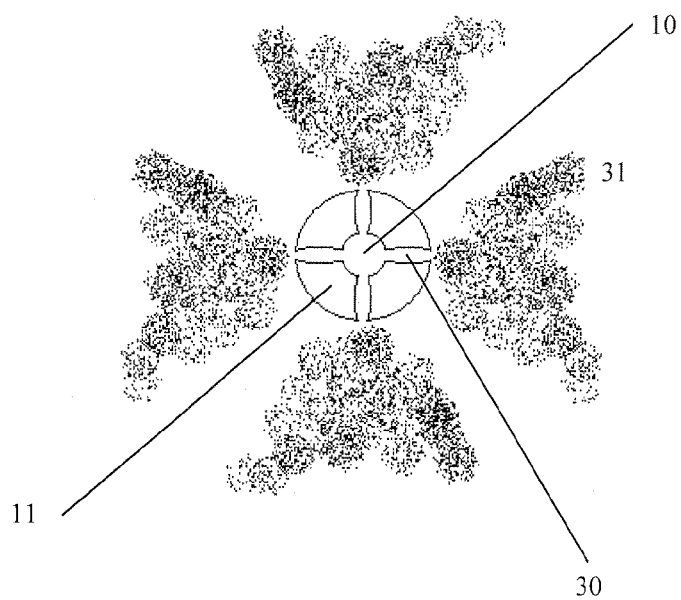
FIG. 6 schematically illustrates a cross section view of another embodiment of the invention.

Referring again to the drawings, FIG. 6 is a schematic diagram illustrating a cross section of an exemplary embodiment of the invention, having two lumens, an internal lumen 10 and an external lumen 11. The figure shows internal lumen 10 having lateral tunneled extensions 30, connecting the internal lumen to an orifice through which fluid can flow outside of the catheter. Referring again to FIG. 6, the outward flow of fluid 31 through four apertures is shown. This is, however, only for the purpose of illustration, and in practice, the device may contain fewer or more than four apertures at each cross-sectional level, as determined by the functional requirements of the device. This flow of fluid enables the catheter to float or hover within the colon, prevents contact between the catheter and the colonic wall, thus reducing friction between them, and is used to break down fecal matter.

Figure 7:
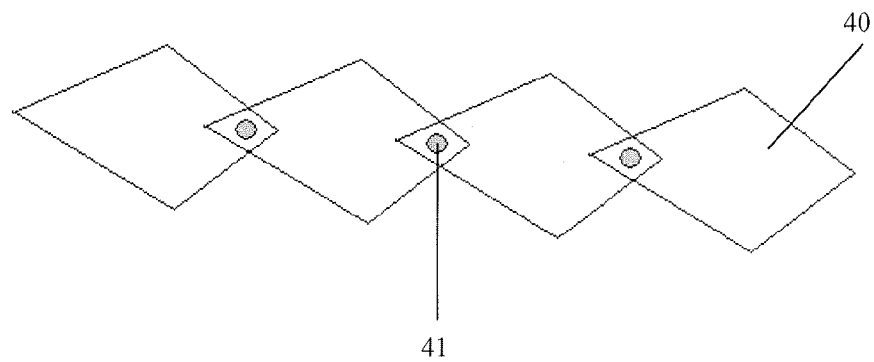
FIG. 7 schematically illustrates a side view of one exemplary embodiment of the invention.

Referring again to the drawings, FIG. 7 is a schematic diagram illustrating a side view of yet another exemplary embodiment of the invention. In this embodiment the device of the invention includes rigid or semi-rigid elements 40, connected between them by hinges 41. In this exemplary embodiment the elements 40 are external to the conduit invention, essentially forming a "shell" therefor. This shell element is advantageous since it combines rigidity, easier advancement of the device into the colon, and hinges that permit advancement of the device through tortuous parts of the colon, and the colonic flexures.

The elements 40 may be of different shapes and different sizes. Exemplary shapes include triangular, cubical, pentagonal, and hexagonal or may have more than six flanks. The shape may be rounded or straight angled. Exemplary sizes range from 2 mm to 50 mm, preferably about 5 mm. Exemplary materials for the elements may be biocompatible metals, biocompatible plastics and biocompatible polymers.

The present invention also provides a method for using the device described hereinabove for cleaning body cavities such as the colon, in a mammalian (preferably human) subject in need of such a procedure. In its most general form, this method comprises the steps of:

a) Introducing the device into the large intestine via the anus and rectum;
b) The pressurized cleaning fluid supply and negative (suction) pressure source is then connected to the proximal end of the conduit of the device, such that:
   a. the head region and at least part of the conduit are caused to float or hover within the colon (or other body passage lumen), thereby significantly reducing frictional contact with the walls thereof during the insertion and advancement of the device;
   b. the walls of the colon are subjected to the cleaning effect of the fluid sprays, even while the device is being inserted and advanced distally;
c) Manual pushing and pulling forces are applied by the operator to the proximal end of the conduit such that distal head region (and said conduit which is attached thereto) advance distally within the colon. This distal (i.e. forward) movement is optionally enhanced by the cleaning liquid jet sprays emanating from backward-pointing jet nozzles. As mentioned above, the cleaning liquid jet sprays (together with the aspiration of the fluid and solid debris) causes the lumen and walls of the large intestine to be cleansed of fecal material as the device is advanced;
d) Optionally, further procedures may be performed at any given location within the colon. These procedures include tissue biopsy, surgical removal of polyps and other lesions, capture of video and still images of the colonic wall and lumen, guiding the distal head unit towards selected portions of the colonic wall in order to increase cleansing efficiency, either by the fluid jet action, or by additional mechanical means, as will be described hereinbelow;
e) The device is then removed from the colon and from the body of the patient. Optionally, the cleaning fluid jets and suction remain operational during the removal stage.

It is to be emphasized that while the above cleaning method has been described with special reference to the human colon, it may also be applied to any other body cavity that will permit introduction and passage of the device of the present invention.

In the embodiments of the invention that have been described so far, said invention is constructed as a stand-alone device, i.e. the conduit and attached distal head are capable of being inserted into the colonic (or other body cavity) lumen, used to cleanse said lumen and/or deliver therapeutic agents and/or remove samples (such as tumor markers), without the need for any ancillary devices or equipment. However, in another preferred embodiment, the device of the present invention may also be inserted into the colon (and removed therefrom) while contained within the working channel of a colonoscope. In this embodiment, the device may be advanced distally of the distal end of the colonoscope in order to expose some or all of the apertures on the head and conduit of the device, thereby permitting cleansing and/or therapeutic agent delivery and/or sample collection of a particular region of the colon. This advancement, and subsequent retraction, of the device of the invention in relation to the colonoscope may be achieved by manual pushing or pulling of the proximal end of the conduit of the device and/or by the use of other directing means, one example of which will be described hereinbelow. In addition, the hovering mechanism effected by the fluid jets leaving the apertures formed in the device's distal head and conduit may be used not only to center the device within the colonic lumen, but also to provide forwardly directed propulsion of the device, instead of, or as an ancillary aid to, the other pushing/pulling means mentioned above.

In this embodiment, the device will generally have a smaller diameter than the stand-alone version described hereinabove, in order to permit its passage through the colonoscope working channel, which typically has a diameter of 3.8 mm. In some cases, the conduit of the present invention will have a diameter considerably smaller than that of the working channel, for example in the order of about 1 mm. The space between the conduit and the walls of the working channel can, in these embodiments, be used as an additional 'virtual channel' for the purposes of the aspiration and removal of fecal material and cleaning fluid from the colon and from the body.

Figure 8:
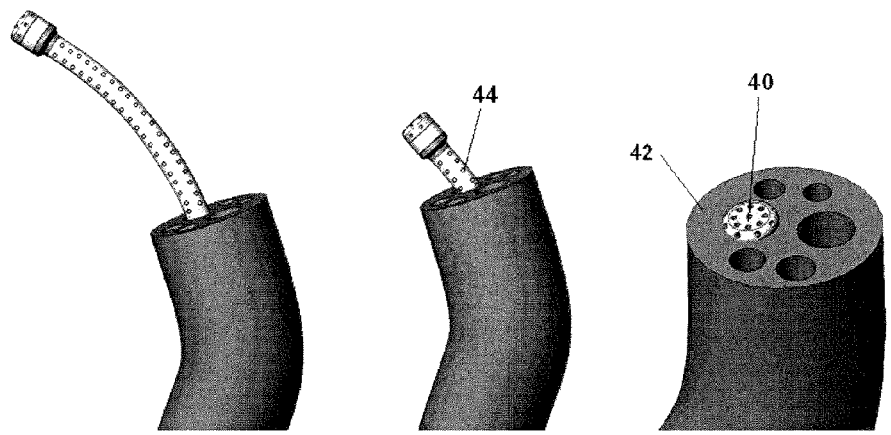
FIG. 8 schematically illustrates a side view of a further embodiment of the invention, which is inserted into the working channel of a colonoscope.

Referring again to the drawings, FIG. 8 depicts the aforementioned embodiment of the present invention, wherein the device of the present invention is introduced into the body cavity through within the working channel of an endoscope, such as a conventional colonoscope. Beginning with the drawing on the right side of FIG. 8, the distal head 40 of a device of the invention may be seen within the distal portion of a working channel of colonoscope 42. The middle drawing shows the device after the head and the distal-most portion of the conduit 44 has been advanced beyond the distal end of the colonoscope. Finally, the drawing on the left side of FIG. 8 depicts a typical situation wherein the exposed portion of the device head and distal part of the conduit are able to perform their washing and aspiration functions within the colonic lumen.

Figure 9:
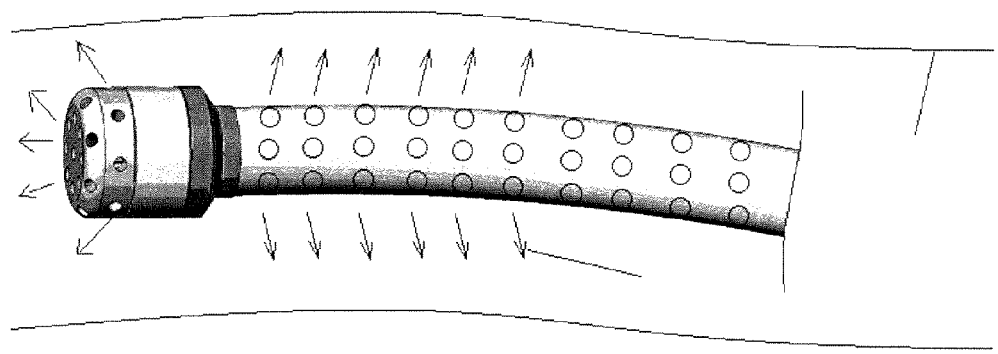
FIG. 9 schematically depicts the manner in which fluid jets leaving the apertures along the conduit and in the distal head may be used for the purposes of hovering, guidance and advancement of the device.

As mentioned above, the hovering, guidance and advancement of the device in relation to the colonoscope may be done using the apertures present along the conduit and distal head of said device. The conduit acts as a "spine" that is rigid enough to be advanced and retracted by manual means (or by use of one or more directing wires as will be described hereinbelow). At the same time, the conduit is sufficiently flexible such that it is able to bend and move in response to the fluid jets. These jets leave the apertures in the conduit and distal head with a certain velocity that is sufficient to impart an impact force on the colon wall, thus causing said distal head and the exposed region of the conduit to hover within the colonic lumen with minimal friction (since there is no direct contact between the tube and the colon). The jets (particularly those in the conduit) may be directed with a slight backwards angle (i.e. in a proximal direction) to enable easier insertion into the colon. The apertures in the distal head portion are mainly used for cleansing using fluid jets and/or for aspiration of feces and liquid remains. The fluid jet directions of a typical device of this embodiment of the present invention (as described above) are indicated by the arrows in FIG. 9.

The present invention also provides a method for using the device described immediately hereinabove for cleaning body cavities such as the colon, in a mammalian (preferably human) subject in need of such a procedure. In its most general form, this method comprises the steps of:
a) Insertion of a standard colonoscope through the anus and rectum of the subject into the colon;
b) Insertion of the device of the present invention into the working channel of the colonoscope;
c) Advancement of the device through the colonoscope working channel in a distal direction, until the distal head region thereof exits the distal end of the working channel of said colonoscope, by means of manual pushing and pulling and, where desired, by means of connecting the pressurized cleaning fluid supply and negative (suction) pressure source to the conduit of the device, such that the head region and at least part of the conduit are caused to float or hover within the working channel of the colonoscope, thereby significantly reducing frictional contact between the device and the walls of said working channel during the advancement of the device;
d) Cleaning the region of the colon that is adjacent to the distal head region and portion of the conduit that has exited the distal end of the working channel of the colonoscope, using the fluid jets and suction created by that region of the device;
e) Optionally, further procedures may be performed at the current location of the distal head region and exposed portion of the conduit within the colon. These procedures include tissue biopsy, surgical removal of polyps and other lesions, capture of video and still images of the colonic wall and lumen, guiding the distal head unit towards selected portions of the colonic wall in order to increase cleansing efficiency, either by the fluid jet action, or by additional mechanical means, as will be described hereinbelow;
f) The colonoscope may then be advanced distally until it reaches the next area of the colon of interest to the operator. This may be done by moving the colonoscope distally over the exposed portion of the conduit and distal head of the device (thereby using this part of the device as a type of 'guidewire'). The distal head region and a desired length of conduit proximal to that region may then be advanced distally by a combination of manual pushing/pulling and jet spray action, until said distal head region reaches the desired location. Alternatively, the exposed portion of the device may be retracted (moved proximally) such that its distal part becomes entirely contained within the working channel of the colonoscope. The colonoscope and the device are then moved together in a distal direction (in relation to the colon) until the desired region is located. The distal head region is then moved distally until it is located at the desired distance from the distal end of the colonoscope;
g) Steps (e) and (f) are then repeated as required;
h) The device and the colonoscope are then removed from the colon and from the body of the patient. Optionally, the cleaning fluid jets and suction remain operational during the removal stage.

It is to be emphasized that while the above cleaning method has been described with special reference to the human colon, it may also be applied to any other body cavity that will permit introduction and passage of the device of the present invention.

As mentioned above, ancillary means for advancing, retracting and directing the distal head and distal regions of the conduit, such as directing wires, may be used. These wires may be similar to the control wires used in the construction of conventional colonoscopes, as well known in the art, and may be made from materials such as nitinol and stainless steel. One example of such means is the directing wire 60 shown in FIG. 10A, the distal end of which is attached to the distal device head. The wire extends proximally, ending beyond the proximal end of the colonoscope (i.e. outside of the patient's body). The wire may pass from its distal attachment to proximal end of the colonoscope by two different routes. In one option, the wire passes between the external surface of the conduit and an over-conduit sheath the purpose of which is to protect both the endoscope and patient's body from frictional contact with the wire. Alternatively, the wire may pass internally from its distal attachment in a proximal direction through one of the internal (i.e. suction and/or irrigation) lumens of the conduit. Manipulation of the proximal end of the wire will enable the operator to guide and direct in any desired direction. Once the device has been pulled by the wire in a particular direct it can then be rotated and pushed/pulled, as illustrated in FIG. 10B. Thus by these means, the distal head may be directed to any point in space within the body that is required.

Figure 10A:
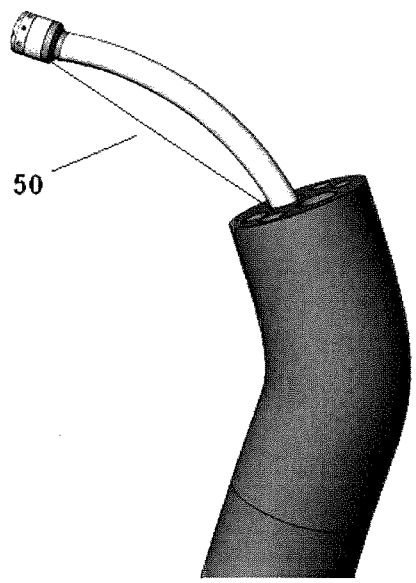
FIGS. 10A and 10B illustrate the use of a directing wire to bend the head and distal part of the embodiment of the device shown in FIG. 8 in various directions.
Figure 10B:
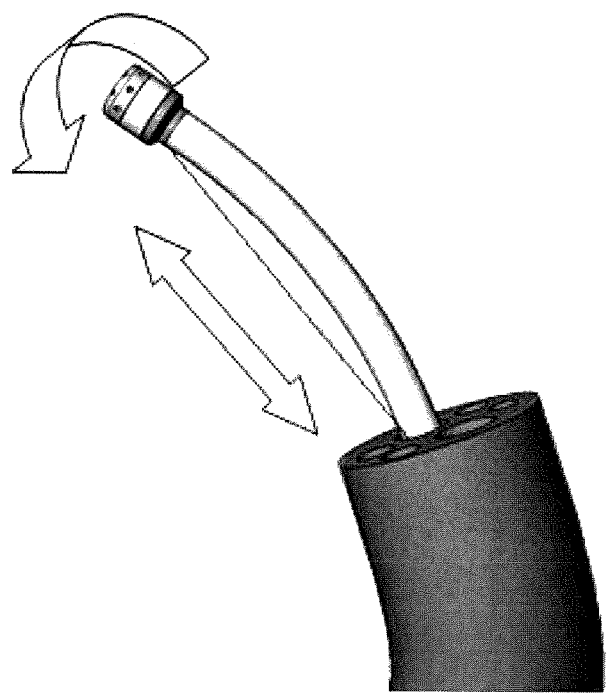

It should be emphasized that although the directing wire shown in FIGS. 10A and 10B is used in connection with the intra-colonoscopic version of the present invention, it is equally possible and desirable to include one or more such wires in the structure of the stand-alone embodiment. In such a case, the wire(s) will pass proximally either through one of the internal lumens of the conduit, or sandwiched between the outer wall of the conduit and an external sheath.

In some cases the fluid jets of the presently-disclosed device will be the sole means for cleansing the colonic lumen. In other embodiments, however, this fluid-pressure cleaning will be supplemented by mechanical cleaning that is implemented by a variety of different elements that are assembled onto the distal portion of the device. Such mechanical cleaning elements include (but are not limited to) disc, brush discs, brushes, stationary fabric strips and fabric strips attached to a rotatable element.

Figure 11:
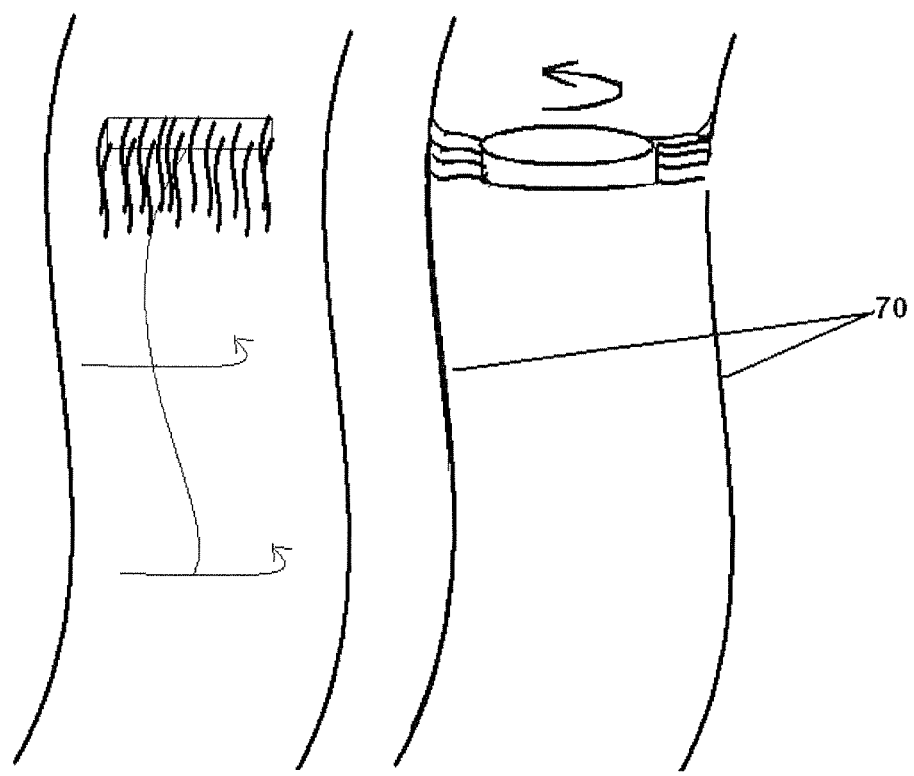
FIG. 11 illustrates one example of additional mechanical cleaning means that may be incorporated into the present device.

FIG. 11 schematically illustrates one example of a brush disc implementation. The brush discs may be typically in the range of 2-10 mm in diameter and have a thickness of 1-2 mm. A series of bristles are attached to the circumference of the discs. The disc may be made of any suitable soft, flexible biocompatible material including (but not limited to) silicon and rubber, while the bristles may be constructed from materials such as fabric fibers, silicon or soft plastic.

In one embodiment, the disc brushes may be pre-assembled around the distal region of the conduit, immediately proximal to the distal head portion of the device. In another embodiment (e.g. when the device of the invention is used from within a colonoscope), the device of the invention is inserted through the colonoscope working channel. In one version, the brush disc may be used to mechanically scrub the colon wall (e.g. by manually or automatically pushing and pulling and/or rotating the conduit of the device), as shown in the left side of FIG. 11. In an alternative embodiment, the brush disc may be connected to a simple DC motor through a 1-2 mm diameter metal wire, and thereby caused to rotate at a frequency in the approximate range of 1-30 hz. As illustrated in FIG. 11, upon rotation of the disc, the brush bristles will become disposed horizontally, and thereby have a large impact area with respect to the colonic contents and colonic wall 70. The bristles may be attached around the entire circumference of the disc. In another embodiment, they may be attached to only certain selected sectors of the circumference. In such cases, an asymmetric distribution of the bristles may be used to generate imbalance in the disc to which they are attached, such that vibratory movements thereof are induced. This vibration may assist the mechanical cleaning effect of the disc and bristles, and thereby cause a more effective disintegration of fecal material in the colon. In order to increase the vibratory effect, small weights may also be attached to the disc or bristles, in order to increase the mass asymmetry of the brush disc. In a further variant of this embodiment, vibratory motion of the head region may also be achieved by attaching a miniature ultrasonic transducer or similar device to said head region.

Figure 12:
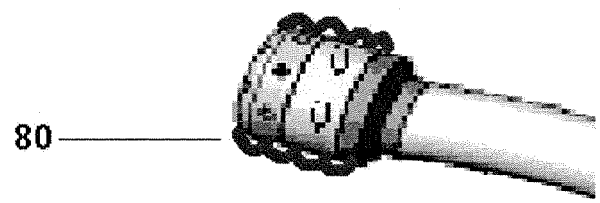
FIG. 12 depicts the use of fabric strips fitted to the head region as an additional mechanical cleaning element.

In another embodiment, the device of the invention further comprises fabric or plastic strips that are firmly attached along the sides of the distal head region of said device. These strips, which may be made from, for example, rubber, silicon fibers, soft plastics and the like, may be attached to the distal head by means of gluing (e.g. with a biocompatible Loctite adhesive), either directly, or through an anchoring hole. In this way, the fabric or plastic strips provide a roughened surface which may be caused to frictionally engage with the fecal debris, thereby breaking down and dislodging said debris. Operationally, it will generally be necessary to direct the distal head region (e.g. using the above-described directional wires), such that it is brought into close contact with the region that requires the use of the additional mechanical abrasion in order to be cleaned. FIG. 12, which schematically depicts one implementation of this embodiment, shows two fabric strips 80 attached to distal head of the device. In an another version of this embodiment (not illustrated), bristles or fibers prepared from similar materials to those described above in the manufacture of the plastic or fabric strips, are embedded in the distal head region of the device, such that they surround the jet spray apertures. These fibers or bristles may be separately prepared and then glued to the distal head region (e.g. using a biocompatible Loctite adhesive). Alternatively, they may be produced as an integral part of the distal head region during the molding process used to manufacture said head region.

Figure 13:
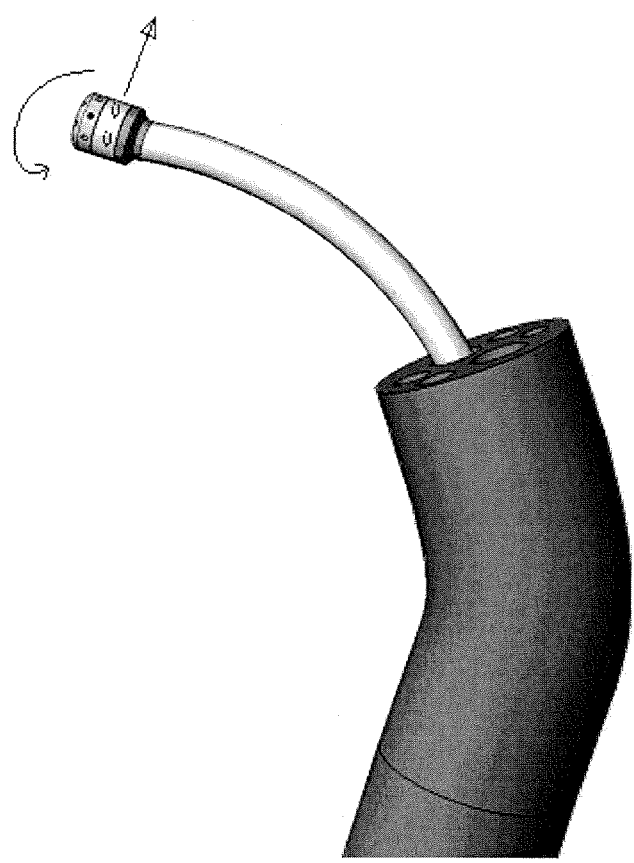
FIG. 13 depicts the use of tangential jet sprays located in the middle section of the distal head as a means of causing high frequency vibration of said head.

In an further embodiment of the present invention, the lateral surface of the distal head of the device comprises one or more apertures which are angled such that they propel a jet of cleaning fluid in a tangential direction (in relation to the circumference of the head). This direction is indicated by the straight arrow in FIG. 13. In this way, high frequency vibration of the device head (and at least part of the conduit) is set up. This vibration, in turn, will cause rapid linear or rotatory movement of the jet wash sprays, thereby assisting them in breaking down the fecal matter.

Figure 14:
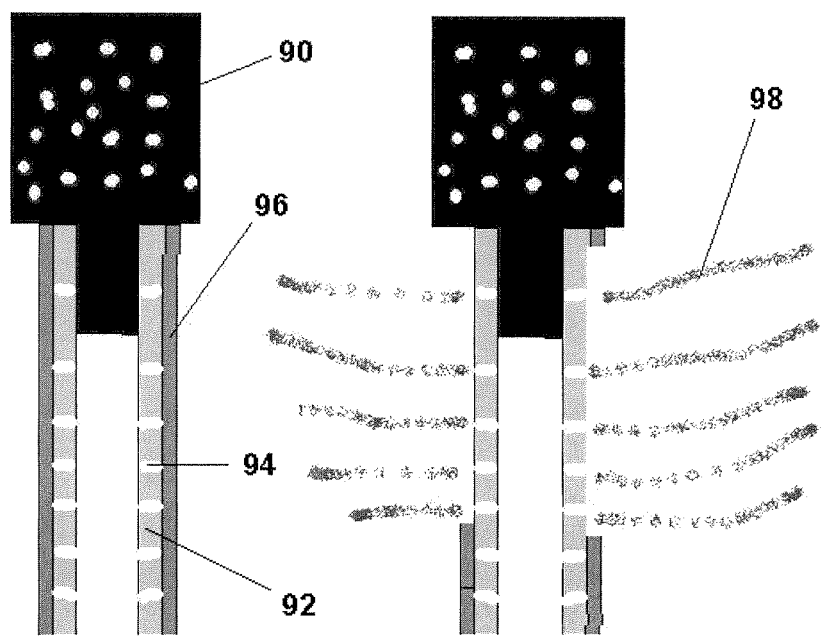
FIG. 14 schematically illustrates an alternative embodiment of the device wherein a sleeve fitted around the conduit may be used to selectively cover or uncover the jet spray apertures located in said conduit.

In a still further embodiment of the stand-alone embodiment of the device of the present invention, said device further comprises a sleeve or sheath that is closely fitted around the conduit. This is illustrated in the left side of FIG. 14, which shows a typical stand-alone implementation of the presently-disclosed device, comprising a distal head region 90, a conduit 92, and jet spray apertures 94 in said conduit. A plurality of apertures is also shown in the head region. A sleeve 96 is shown covering the conduit, thereby blocking the jet spray apertures. A retraction device (e.g. one or more wires; not shown) is attached to the proximal end of sleeve 96, such that the sleeve may be partially withdrawn (i.e. in a proximal direction, thereby selectively exposing a certain number of jet spray apertures. Consequently, by these means it is possible to use the device with the lateral apertures disabled (i.e. covered by the sheath), as shown in the left side of FIG. 14, and then to control the degree of spray 98 from the conduit region, by partially withdrawal of the sheath, as depicted in the right side of FIG. 14. The sheath may be constructed of any suitable biocompatible material including, but not limited to, silicone, polyurethane, Pebax and nylon.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the invention as claimed.

The invention claimed is:

1. A device suitable for insertion into a body passage, comprising a conduit and a distal head region located at the distal end of said conduit,
    wherein said conduit and said distal head region comprise at least one common internal lumen,
    wherein said at least one common internal lumen is in fluid communication with a plurality of apertures that are located on the external surface of the distal head region and on the external surface of a portion of said conduit proximal to said distal head region,
    wherein at least some of the apertures in the conduit and distal head region are adapted such that a fluid pumped through said at least one lumen in a proximal-to-distal direction would exit said apertures in the form of a jet spray;
    wherein said conduit is sufficiently flexible such that it is able to bend and move in response to said jet spray.

2. The device according to claim 1, wherein said jet spray apertures are spatially arranged such that if the device were to be placed in a body passage and a jet spray caused to exit said jet spray apertures, said device would be caused to have minimal contact with the walls of said body passage.

3. The device according to claim 2, wherein the jet spray apertures are arranged in a symmetrical manner around the circumference of an imaginary transverse section of said device.

4. The device according to claim 2, wherein the jet spray apertures are arranged such that at least one of said apertures is to be found in each of the four quadrants of the circumference of an imaginary transverse section of said device.

5. The device according to claim 1, wherein at least some of the apertures in the conduit and distal head region are capable of aspirating a liquid situated external to said device upon connection of a negative pressure source to the one or more lumens connected to said apertures.

6. The device according to claim 1, further comprising mechanical cleaning elements attached to the conduit and/or distal head region.

7. The device according to claim 6, wherein the mechanical cleaning elements are selected from the group consisting of discs, brushes, disc brushes, bristles and fabric strips.

8. The device according to claim 1, further comprising guiding means for changing the spatial location of the distal head region.

9. The device according to claim 8, wherein the guiding means comprises one or more wires attached to the distal head region.

10. The device according to claim 1, wherein said device comprises two internal lumens.

11. The device according to claim 1, further comprising one or more cameras attached to its external surface.

12. The device according to claim 1, further comprising an internal lumen containing an optical fiber bundle.

13. The device according to claim 1, further comprising a working channel.

14. The device according to claim 1, wherein the apertures are located in the distal head region and along the entire length of the conduit.

15. The device according to claim 1, wherein the apertures are located in the distal head region and at least 20% of the length of the conduit.

16. A method for cleansing the lumen of a body passage in a mammalian subject, comprising the steps of:
    a) introducing a device according to any of the previous claims into said body passage;
    b) connecting a pressurized cleaning fluid supply and negative pressure source to the proximal end of the conduit of said device, such that fluid jet spray exiting the jet spray apertures cause the distal head region and at least part of said conduit to hover within the body passage lumen with minimal contact with the walls therefore, and such that said fluid jet spray causes displacement, dislodgement, disintegration and/or dissolution of solid matter present within said body passage, and such that the jet spray liquid and solid and particulate matter within said body passage is removed from the lumen thereof by aspiration through at least some of the apertures in said device;
    c) applying manual pushing and pulling forces to the proximal end of the conduit such that said device advances distally within said body passage;
    d) optionally performing further procedures within the body cavity,
    e) removing said device from said body passage.

17. The method according to claim 16, wherein the optionally-performed procedures are selected from the group consisting of tissue biopsy, surgical removal of polyps and other lesions, capture of video and still images of the colonic wall and lumen, and guiding the distal head region towards selected portions of the colonic wall in order to increase cleansing efficiency.

18. A method for cleansing the lumen of a body passage in a mammalian subject, comprising the steps of:
    a) inserting an endoscope into said body passage;
    b) inserting a device according to claim 1, into the working channel of the colonoscope;
    c) advancing said device through said working channel until the distal head thereof exits the distal end of said working channel, by means of manual pushing and pulling, and optionally by means of connecting the pressurized cleaning fluid supply and negative (suction) pressure source to the conduit of the device, such that the head region and at least part of the conduit are caused to float or hover within the working channel of the colonoscope, thereby significantly reducing frictional contact between the device and the walls of said working channel during the advancement of the device;
    d) cleaning the region of the colon that is adjacent to the distal head region and portion of the conduit that has exited the distal end of the working channel of the colonoscope, using the fluid jets and suction created by that region of the device;
    e) advancing the colonoscope distally to a new region of interest;
    f) repeating steps (c) to (e), as required;
    g) removing said device from said body passage.

19. The method according to claim 16, wherein the body passage is the colon.

20. The method according to claim 16, wherein said method is used prior to a colonoscopic procedure.

21. A system for colonic cleansing comprising:
a) a device according to claim 1,
b) a pump suitable for causing said cleaning fluid to pass distally through one or more lumens of said device and to exit through a plurality of jet spray apertures;
c) a negative pressure source; and
d) optionally further comprising a user interface for controlling the operation of said device, said pump and said negative pressure source.

* * * * *